(12) United States Patent
Hickling

(10) Patent No.: US 8,203,909 B1
(45) Date of Patent: Jun. 19, 2012

(54) FORWARD-LOOKING SONAR FOR SHIPS AND BOATS

(76) Inventor: Robert Hickling, Huntington Woods, MI (US)

( * ) Notice: Subject to any disclaimer, the term of this patent is extended or adjusted under 35 U.S.C. 154(b) by 187 days.

(21) Appl. No.: 12/800,169

(22) Filed: May 10, 2010

Related U.S. Application Data

(63) Continuation-in-part of application No. 10/396,541, filed on Mar. 25, 2003, now Pat. No. 7,058,184, and a continuation-in-part of application No. 10/746,763, filed on Dec. 26, 2003, now Pat. No. 7,054,228, and a continuation-in-part of application No. 10/842,880, filed on May 10, 2004, now Pat. No. 7,054,226, and a continuation-in-part of application No. 11/607,376, filed on Dec. 2, 2006, now Pat. No. 7,920,709.

(51) Int. Cl.
*G01S 15/88* (2006.01)
(52) U.S. Cl. ............................................ 367/88; 367/87
(58) Field of Classification Search ................... 367/87, 367/88
See application file for complete search history.

(56) References Cited

U.S. PATENT DOCUMENTS

| | | | | |
|---|---|---|---|---|
| 4,216,537 A | * | 8/1980 | Delignieres | 367/88 |
| 4,236,040 A | * | 11/1980 | Chung | 73/646 |
| 5,537,366 A | * | 7/1996 | Gilmour | 367/88 |
| 5,546,356 A | * | 8/1996 | Zehner | 367/88 |
| 7,054,226 B1 | | 5/2006 | Hickling | |
| 7,058,184 B1 | | 6/2006 | Hickling | |
| 2007/0025183 A1 | * | 2/2007 | Zimmerman et al. | 367/88 |

OTHER PUBLICATIONS

U.S. Appl. No. 11/607,376, filed Dec. 2, 2006, Robert Hickling.
R. Hickling et al, "Use of pitch azimuth plots in determining the direction of a sound source in water." J. Acoust. Soc. Am., 97, 856-865, 1995.

* cited by examiner

*Primary Examiner* — Ian Lobo
(74) *Attorney, Agent, or Firm* — Reising Ethington P.C.

(57) ABSTRACT

Method and apparatus for detecting and locating underwater obstacles in the path of a ship or boat. The apparatus includes a pulsed wide-angle sonar projector (100) controlled by a digital signal processor (400) that emits sound pulses at frequencies of 30 kHz and less that can penetrate sediment-laden water hundreds of meters or more ahead of the ship or boat. The projector generates echoes from submerged objects. A vector sound-intensity probe (200) receives the echoes and transmits them to the digital signal processor. The digital signal processor determines the location of submerged obstacles ahead of the ship or boat from the echoes received by the probe. This information is displayed on an output device (500). The sonar projector and vector sound-intensity probe are contained separately in streamlined housings aimed in the forward direction under the bow of the ship or boat. The processor, output device and other electronics are located on board the ship or boat.

14 Claims, 4 Drawing Sheets

FORWARD-LOOKING SONAR FOR SHIPS AND BOATS

THIS APPLICATION IS A CONTINUATION-IN-PART OF U.S. patent application Ser. No. 10/396,541, filed Mar. 25, 2003, ENTITLED "ACOUSTIC MEASUREMENT METHOD AND APPARATUS", U.S. Pat. No. 7,058,184, issued Jun. 6, 2006, OF U.S. patent application Ser. No. 10/746,763, filed Dec. 26, 2003, ENTITLED "SOUND SOURCE LOCATION AND QUANTIFICATION USING VECTOR PROBES" U.S. Pat. No. 7,054,228, issued May 30, 2006, OF U.S. patent application Ser. No. 10/842,880, filed May 10, 2004, ENTITLED "METHOD AND APPARATUS FOR ECHOLOCATION", U.S. Pat. No. 7,054,226, issued May 30, 2006, OF CONTINUATION-IN-PART ENTITLED "VECTOR SOUND-INTENSITY PROBES OPERATING IN A HALF SPACE" Ser. No. 11/607,376 FILED 2006 Dec. 2 now U.S. Pat. No. 7,920,709. BY ROBERT HICKLING, THE PRESENT INVENTOR.

TECHNICAL FIELD

This invention relates to a sonar system at the bow of a ship or boat for detecting underwater obstacles.

BACKGROUND OF THE INVENTION

1. U.S. Pat. No. 7,054,226 May 30, 2006 issued to R. Hickling entitled "Method and Apparatus for Echolocation", discloses the use of the vector sound-intensity probe and ultrasound in air for applications such as robot guidance, aids to the blind, and simulating bat sonar. Use of the vector sound-intensity probe is an important part of the present invention. Sound intensity is sound-power flow per unit area. There are two types of vector sound-intensity probe: a full-space probe that measures vector sound intensity in three dimensions, described in 2. R. Hickling, "Acoustic Measurement method and apparatus" U.S. Pat. No. 7,058,184 Jun. 6, 2006 which is hereby incorporated herein by reference; and a half-space vector probe that measures sound intensity in the half space above the ground or next to a wall, described in 3. R. Hickling, "Vector sound-intensity probes operating in a half space", patent application Ser. No. 11/607,376, Dec. 2, 2006.

which is hereby incorporated herein by reference. The half-space probe is used in the present invention to measure vector sound intensity ahead of the boat or ship.

Vector probes in water have been shown to measure direction accurately, as demonstrated in 4. R. Hickling and W. Wei, "Use of Pitch Azimuth Plots in Determining the Direction of a Sound Source in Water with a Vector Sound-Intensity Probe", Journ. Acoust. Soc. Amer., 97, 856-865. 1995.

What is needed is a device that uses low frequency sound in water to enable ships and boats to avoid underwater obstacles. Low-frequency sound at about 30 kHz and below is required to penetrate sediment-laden water ahead of the ship or boat. This is particularly important in riverine and littoral environments. Fish finders, acoustic cameras and narrow-beam search devices operate at higher frequencies and are incapable of penetrating very far in sediment-laden water.

SUMMARY OF THE INVENTION

The forward-looking sonar system for ships and boats has two components: (a) a pulsed wide-angle sonar projector and (b) a half-space, vector sound-intensity probe. These are connected to a digital signal processor. The projector generates echoes from submerged obstacles ahead of the ship or boat, which are received by the half-space vector probe. The digital signal processor controls the pulses from the projector and computes vector sound-intensity from the echoes received by the probe. The computer information is displayed on a suitable output device. The frequency of the pulses from the sonar projector has to be such that the pulses can penetrate sediment-laden water ahead of the ship or boat, for distances of hundreds of meters or more.

As described in patent application Ser. No. 11/607,373 incorporated herein by reference, the half-space vector probe consists of four omnidirectional hydrophones positioned at the vertices of an imaginary regular tetrahedron. The lines joining the mid points of the edges of a regular tetrahedron form a Cartesian set of XYZ axes. The origin of these axes is the measurement point of the sound-intensity vector computed by the signal processor. The Z-axis is the central axis of the probe and points in the probe's forward direction.

A half-space vector probe detects sound from the forward half of the surrounding space. Behind the probe is a solid concave axisymmetric structure lined with sound-absorbing material that is open in the probe's forward direction. This prevents noise intrusion from behind the probe. The axis of the structure coincides with the central axis of the probe. The structure can be attached to a back-plate that supports the four hydrophones of the probe.

The pulsed wide-angle projector and the vector sound-intensity probe are each contained in a streamlined, torpedo-shaped housing. The pulsed wide-angle projector and the vector sound-intensity probe both have the same central axis as their respective housings. The housings and their contents point in the forward direction of the motion of the ship or boat and are located beneath the bow. The processor and other electronics are located on board the ship or boat.

DESCRIPTION OF THE PREFERRED EMBODIMENT

Figure 1:
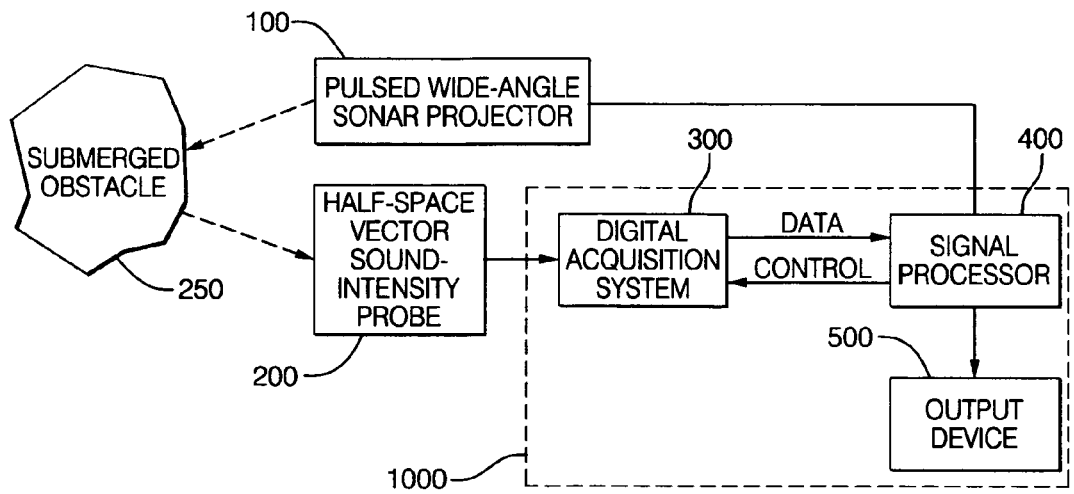
FIG. 1 is a block diagram of a system for detecting obstacles in the path of the ship and boat using a pulsed wide-angle sonar projector and a half-space vector sound-intensity probe.

FIG. 1 is a block diagram showing the different components of the forward-looking sonar for ships and boats. A signal processor 400 drives a pulsed, wide-angle sonar projector 100. The projector 100 operates at frequencies of roughly 30 kHz and below, in order to penetrate sediment-laden water for distances of hundreds of meters or more. The projector 100 generates echo pulses from submerged obstacles 250 that are received by a half-space, vector sound-intensity probe 200. The probe 200 is linked, by means of a digital-acquisition system 300, to a digital signal processor 400. The signal processor 400 uses the echoes received by the probe 200 to detect and determine the location of submerged obstacles 250 ahead of the ship or boat. This information is displayed on an output device 500. The distance and direction of an object determine its location. Distance is calculated using time-of-flight and the sound-intensity vector determines direction. The sonar projector 100 and vector sound-intensity probe 200 are located under the bow of the ship or boat while the electronic system 1000 is operated on board.

Figure 2:
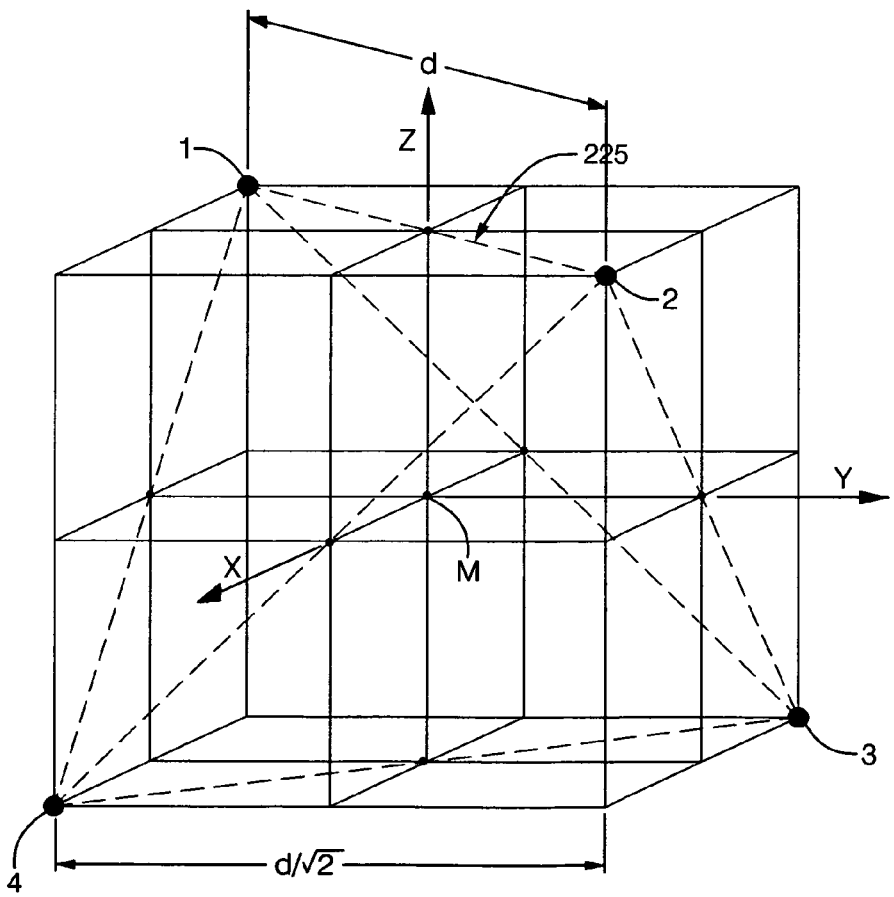
FIG. 2 is a geometric drawing of the locations of the four hydrophones of the half-space vector sound-intensity probe, positioned at the vertices of a regular tetrahedron. The lines joining the midpoints of the edges of the tetrahedron form Cartesian XYZ coordinate axes. The Z-axis points in the forward direction of the probe. The origin is the measurement point
Figure 3:
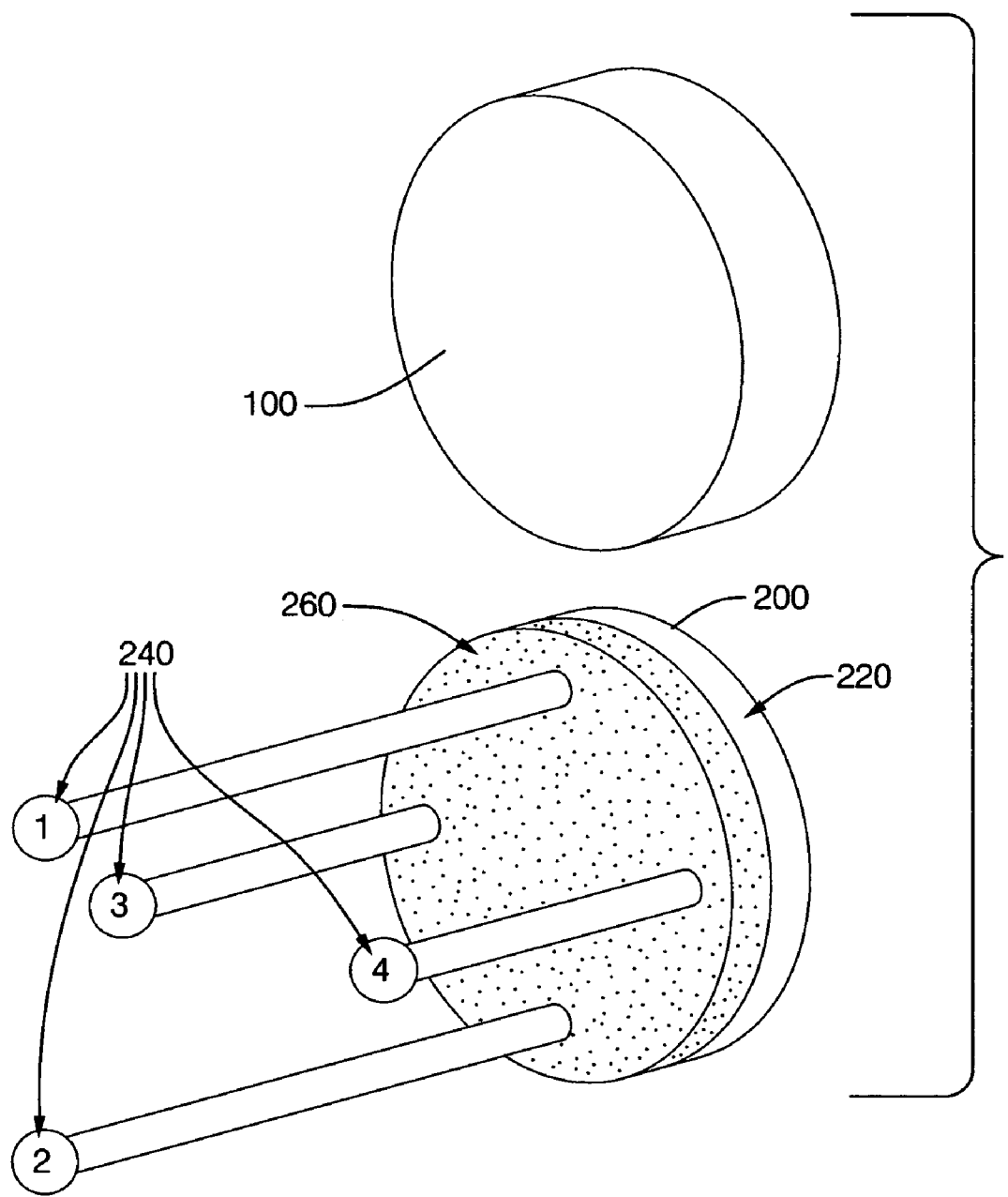
FIG. 3 is a schematic view of a half-space vector sound-intensity probe, with four spherical hydrophones attached to a back-plate with narrow tubes that contain electrical wiring. A sound-absorbing layer is shown attached to the back-plate; between the back plate and the hydrophones. In the figure included above the probe in is a view of a wide-angle sonar projector.

FIG. 2 is a geometric drawing showing the locations of the four hydrophone 1, 2, 3 and 4 of the vector sound-intensity probe 200, at the vertices of a regular tetrahedron 225. The dashed lines are the four edges of the tetrahedron of length d. The lines joining the mid points of the edges form a Cartesian XYZ coordinate system whose origin is the measurement point M. The Z-axis is the central axis of the vector probe, pointing in the forward direction. The theory underlying the use of vector sound-intensity probes is given in References 2 and 3. FIG. 3 is a schematic view of the half-space vector sound-intensity probe 200, showing four omnidirectional spherical hydrophones 240 at the locations 1,2,3 and 4. The figure shows the hydrophones 240 attached to a back-plate 220 by narrow tubes that contain electrical wiring. Between the hydrophones 1, 2, 3 and 4 and the back-plate is a sound-absorbing layer 260. The wide-angle sonar projector 100 is shown separately above the vector probe 200.

Figure 4:
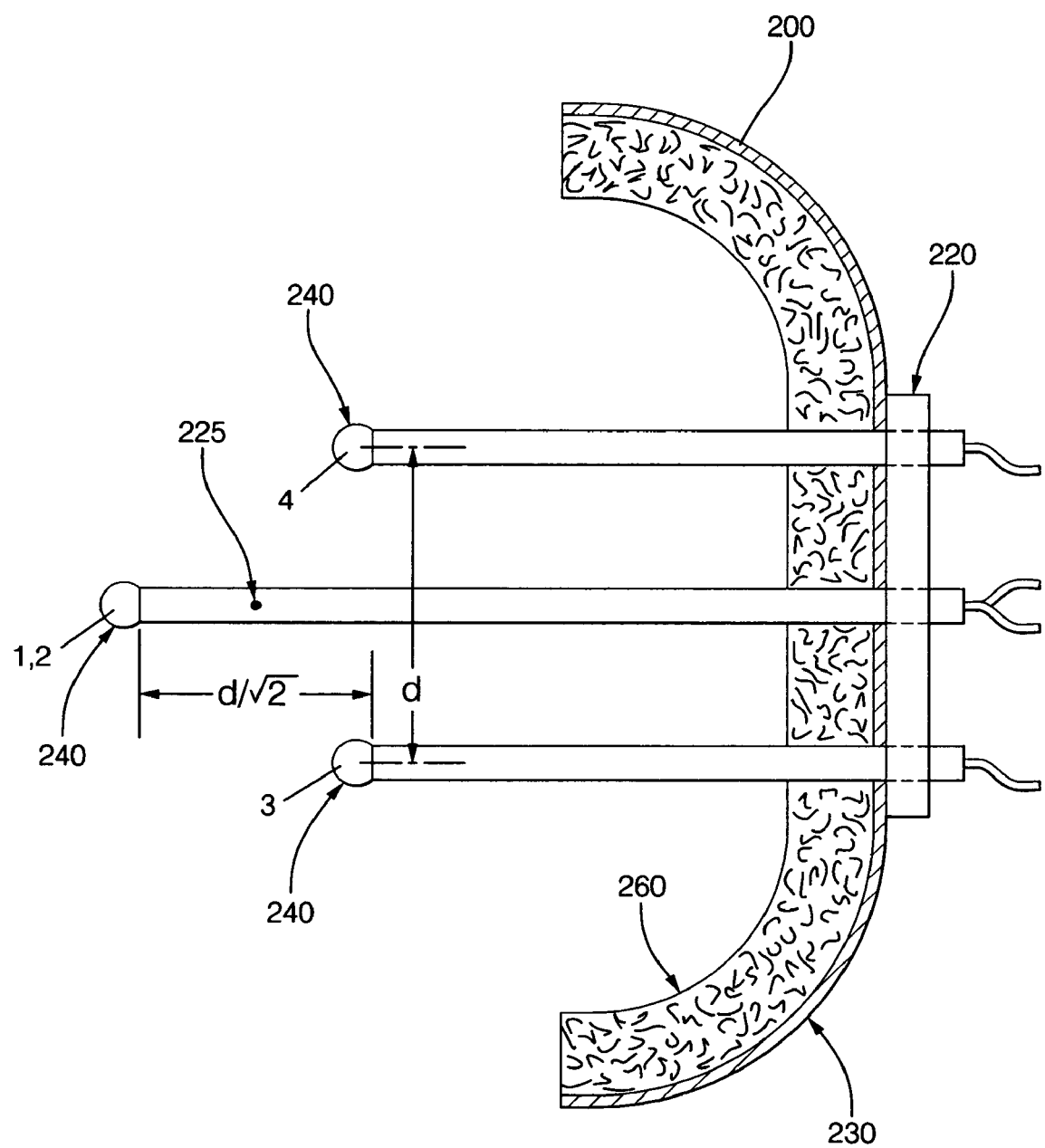
FIG. 4 is a side view of a half-space vector probe with a solid concave barrier lined with absorbing material that prevents noise interference from behind the probe.

FIG. 4 is a side-view of the half-space, vector sound-intensity probe 200, with a concave solid shell 230 lined with absorbing material 260 behind the probe. The shell 230 is circularly symmetric and is attached to the front of the back plate 220. The shell's axis coincides with central axis of the probe. The measurement point is at 225.

Measurement calculations performed by the processor 400 are based on finite-difference approximations that are satisfied when the quantity $2\pi d$ is less than the wavelength of the sound from the sonar projector 100. If this condition is not satisfied, heterodyning, as described in Reference 1, can increase or diminish the wavelength to satisfy the condition.

Figure 5:
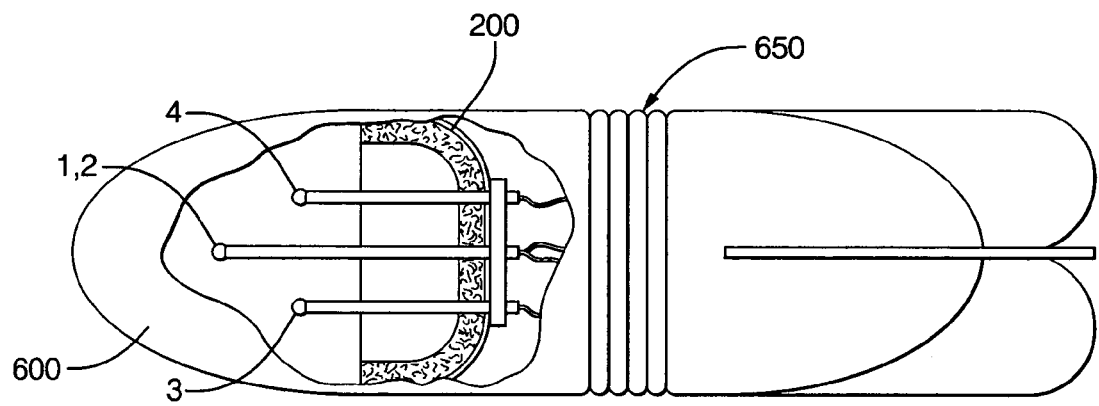
FIG. 5 shows the streamlined, torpedo-shaped housing for a half-space vector probe. The housing is required to reduce flow noise.

FIG. 5 shows a side-view of the half-space vector sound-intensity probe 200 inside a torpedo-shaped, streamlined housing 600. The housing has deturbulator ridges 650 that extend laminar flow over the housing, reducing turbulence and flow noise. The pulsed, wide-angle sonar projector 100 is contained in a similar streamlined housing. Streamlined housings in water generally consist of plastic shells filled with oil that have a sound transmission substantially the same as water.

Figure 6:
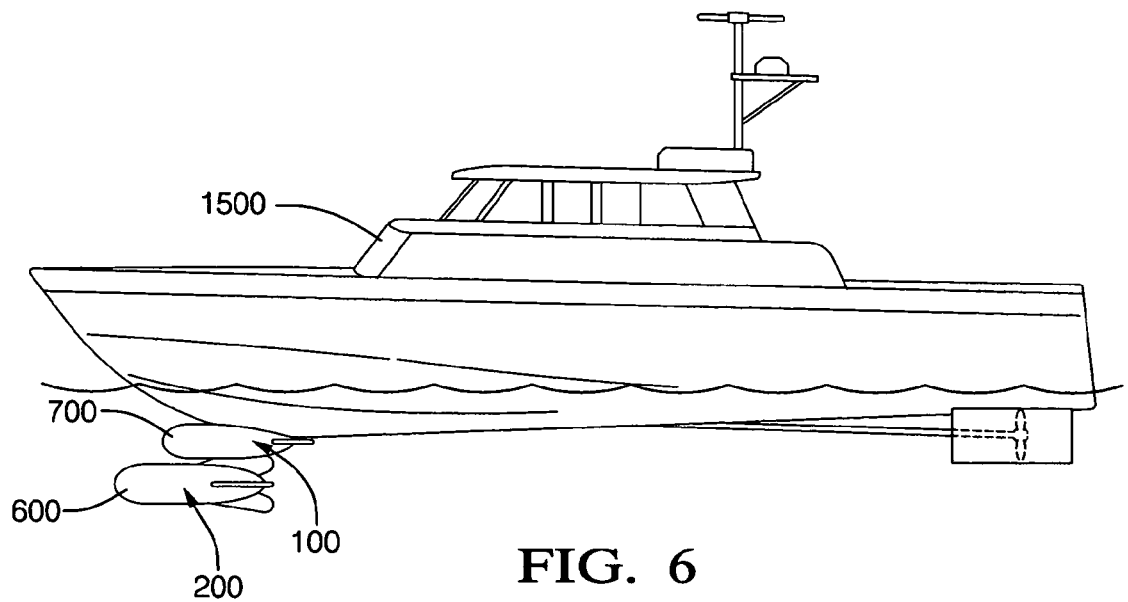
FIG. 6 shows individual streamlined, torpedo-shaped housings for the half-space vector probe and the sonar projector located beneath the bow of a boat.

FIG. 6 shows the torpedo-shaped housing 700 of the pulsed wide-angle sonar projector 100 and the torpedo-shaped housing 600 of the half-space vector sound-intensity probe 200 located beneath the bow of a boat 1500. The digital processor and other electronics are located on board the boat. These locations are the same for a ship.

While the invention has been described by reference to certain preferred embodiments, it should be understood that numerous changes could be made within the spirit and scope of the inventive concepts described. Accordingly it is intended that the invention not be limited to the disclosed embodiments, but that it have the full scope permitted by the language of the following claims.

I claim:

1. An apparatus for a forward-looking sonar system for ships and boats comprising:
a pulsed wide-angle sonar projector that generates echoes from submerged obstacles;
a half-space vector sound-intensity probe that receives said echoes from submerged obstacles;
said half-space acoustic vector sound-intensity probe being in front of and in proximity of a surface that has sound insulating properties to limit sound measurement to only space in front of and bounded by said surface in a forward direction from said apparatus away from said surface;
said surface being concave and axisymmetric with respect to said half-space acoustic vector sound-intensity probe;
a digital signal processor controlling said pulsed wide-angle sonar projector;
a digital acquisition system that conveys echo data from said half-space vector sound-intensity probe to said digital signal processor;
said digital signal processor computing vector sound-intensity from said echo data;
an output device for said digital signal processor.

2. The invention as in claim 1 wherein said pulsed wide-angle sonar projector generates sound of frequency about 30 kHz or less that can penetrate sediment-laden water ahead of said ships and boats for distances of hundreds of meters or more.

3. The invention as in claim 1 wherein said half-space vector sound-intensity probe comprises four omnidirectional hydrophones located at the vertices of an imaginary regular tetrahedron.

4. The invention as in claim 3 wherein the components of said sound-intensity vector are computed relative to Cartesian XYZ axes formed by the lines joining the mid points of opposite edges of said imaginary tetrahedron, the origin of said Cartesian axes being the measurement point; the Z axis pointing in the forward direction of said vector sound-intensity probe.

5. The invention as in claim 3 wherein said half-space vector sound-intensity probe includes a support structure for said four omnidirectional hydrophones that may be a back-plate, where said four omnidirectional hydrophones are located at the ends of four narrow tubes containing electrical wiring that are attached to said back-plate.

6. An apparatus for a forward-looking sonar system for ships and boats comprising:
a pulsed wide-angle sonar projector that generates echoes from submerged obstacles;
a half-space vector sound-intensity probe that receives said echoes from submerged obstacles;
a digital signal processor controlling said pulsed wide-angle sonar projector;
a digital acquisition system that conveys echo data from said half-space vector sound-intensity probe to said digital signal processor;

said digital signal processor computing vector sound-intensity from said echo data;
an output device for said digital signal processor;
wherein said half-space vector sound-intensity probe comprises four omnidirectional hydrophones located at the vertices of an imaginary regular tetrahedron; and
wherein said half-space vector sound-intensity probe includes a solid, concave, axisymmetric structure lined with sound absorbing material that prevents interference by sound from behind said half-space vector sound-intensity probe.

7. The invention as in claim 6 wherein said solid concave structure is attached to a back-plate.

8. The invention as in claim 6 wherein said solid concave axisymmetric structure opens towards said half-space vector probe from behind, the axis of said structure coinciding with the forward direction of the probe.

9. The invention as in claim 1 wherein said pulsed wide-angle sonar projector is contained in a streamlined, torpedo-shaped housing that has the same central axis as said pulsed wide-angle sonar projector.

10. The invention as in claim 9 wherein said streamlined, torpedo-shaped housing containing said pulsed wide-angle sonar projector is located beneath the bow of said ship or boat and points in the forward direction of said ship or boat.

11. The invention as in claim 1 wherein and said half-space vector sound-intensity probe is contained in a streamlined, torpedo-shaped housing that has the same forward axis as said half-space vector sound-intensity probe.

12. The invention as in claim 11 wherein said streamlined torpedo-shaped housing containing said half-space vector sound-intensity probe is located beneath the bow of said ship or boat and points in the forward direction of said ship or boat.

13. The invention as in claim 1 wherein said digital acquisition system, said digital signal processor and said output device are located on board the said ship or boat.

14. A method for detecting the presence and location of underwater obstacles in the path of ships and boats, comprising the steps:
   a. a wide-angle sonar projector emitting underwater sound pulses ahead of said ships and boats and generating echo pulses from underwater objects;
   b. said echo pulses received by a half-space vector sound-intensity probe that is in front of and in proximity to a surface that has sound insulating properties to limit sound measurement to said only space in front of and bounded by said surface in a forward direction away from said surface, said surface being concave and axisymmetric with respect to said half-space vector sound-intensity probe, said echo pulses being transmitted to a digital signal processor; and
   c. said digital signal processor determining the location of said underwater obstacles using time-of-flight and vector direction of said echo pulses.

* * * * *